(12) United States Patent
Kopperschmidt

(10) Patent No.: US 10,751,460 B2
(45) Date of Patent: Aug. 25, 2020

(54) METHOD OF FLUSHING A DIALYZER

(71) Applicant: FRESENIUS MEDICAL CARE DEUTSCHLAND GMBH, Bad Homburg (DE)

(72) Inventor: Pascal Kopperschmidt, Dittelbrunn (DE)

(73) Assignee: FRESENIUS MEDICAL CARE DEUTSCHLAND GMBH, Bad Homburg (DE)

(*) Notice: Subject to any disclaimer, the term of this patent is extended or adjusted under 35 U.S.C. 154(b) by 0 days.

(21) Appl. No.: 15/515,269

(22) PCT Filed: Sep. 29, 2015

(86) PCT No.: PCT/EP2015/001925
§ 371 (c)(1),
(2) Date: Mar. 29, 2017

(87) PCT Pub. No.: WO2016/050353
PCT Pub. Date: Apr. 7, 2016

(65) Prior Publication Data
US 2017/0216512 A1 Aug. 3, 2017

(30) Foreign Application Priority Data
Sep. 30, 2014 (DE) .......................... 10 2014 014 535

(51) Int. Cl.
*A61M 1/36* (2006.01)

(52) U.S. Cl.
CPC ........ *A61M 1/3643* (2013.01); *A61M 1/3626* (2013.01); *A61M 1/3644* (2014.02); *A61M 2205/3306* (2013.01); *A61M 2205/3317* (2013.01); *A61M 2205/3375* (2013.01)

(58) Field of Classification Search
None
See application file for complete search history.

(56) References Cited

U.S. PATENT DOCUMENTS

| 5,591,344 | A | * | 1/1997 | Kenley | ...... A61L 2/04 210/636 |
|---|---|---|---|---|---|
| 2007/0079688 | A1 | | 4/2007 | Okuyama et al. | |
| 2010/0133189 | A1 | * | 6/2010 | Maierhofer | ...... A61M 1/1656 210/644 |
| 2014/0217027 | A1 | | 8/2014 | Meyer et al. | |

FOREIGN PATENT DOCUMENTS

| DE | 10128278 | 9/2002 |
|---|---|---|
| DE | 102008005516 | 2/2009 |
| DE | 102010032980 | 2/2012 |
| WO | WO 2013/019994 | 2/2013 |
| WO | WO 2014/144909 | 9/2014 |

* cited by examiner

*Primary Examiner* — Bradley R Spies
(74) *Attorney, Agent, or Firm* — Jacobson Holman, PLLC.

(57) ABSTRACT

The present invention relates to a method of flushing a dialyzer with a flushing liquid, wherein the dialyzer is arranged in a dialyzate-side circuit of a blood treatment device and wherein the dialyzer has at least one dialyzate-side chamber which has at least one inlet and at least one outlet for the flushing liquid and which is flowed through by the flushing liquid, wherein at least one property of the flushing liquid is measured at the outlet of the dialyzer or downstream of the dialyzer in the dialyzate-side circuit to obtain one or more outlet-side measured values, wherein the property depends on the quantity of the air in the flushing liquid.

5 Claims, 1 Drawing Sheet

METHOD OF FLUSHING A DIALYZER

Figure 1:
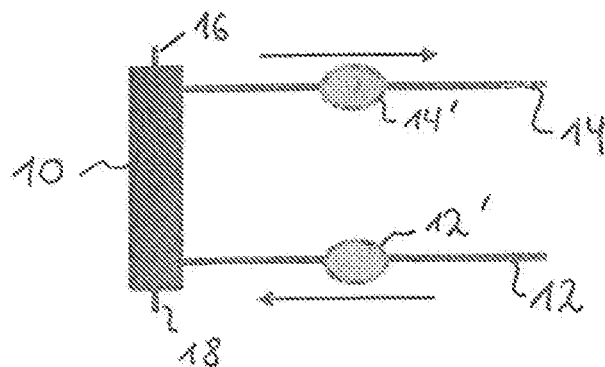

The present invention relates to a method and to an apparatus for flushing a dialyzer. The invention furthermore relates to a blood treatment device having such an apparatus.

Dialyzers for carrying out a blood treatment known from the prior art in general have a dialyzate-side chamber and a blood-side chamber which are separated from one another by a plurality of hollow fiber membranes. In this respect, within the framework of the blood treatment, the blood flows through the interior of the hollow fibers, while the region of the dialyzer surrounding them is flowed around by a dialysis solution.

As a rule, the dialyzers each have an inlet and an outlet both for the dialyzate-side chamber and for the blood-side chamber. Blood or a dialysis solution is respectively supplied to or drained off from the dialyzer through these inlets and outlets respectively.

Disposable dialyzers are as a rule packed in a sterile and dry manner. Before starting a dialysis treatment, they have to be flushed both from the blood side and from the dialyzate side to remove blood from the blood-side chambers and from the dialyzate-side chambers. During the flushing of the extracorporeal circuit, i.e. of the blood circuit, before the start of a dialysis treatment, the still dry hose system is filled with dialysis solution or with sodium chloride via the arterial hose segment and is flushed. The air which escapes in this respect from the hose system or from the blood-side chamber of the dialyzer is drained off into an empty flushing bag or via a corresponding port of the dialysis system or of the blood treatment device via the venous hose system. The blood-side chamber of the dialyzer is thus vented via the connected extracorporeal hose system which is connected to the patient during the treatment and through which blood is conducted from the patient to the dialyzer and back from the dialyzer to the patient.

The dialyzate-side chamber of the dialyzer is vented via the connected hydraulics, i.e. via the dialyzate-side circuit or its components. This dialyzate-side circuit has at least one line which is connected to the inlet of the dialyzate-side chamber and has at least one line which is connected to the outlet of the dialyzate-side chamber of the dialyzer. The dialysis solution is transported to the dialyzer and from the dialyzer through these lines in the operation of the blood treatment device.

It is also possible to transport the air in the dialyzate-side chamber over the membrane provided that the membrane has not yet been wetted.

To vent the dialyzer, the dialyzate-side chamber of the dialyzer can be vented before the blood-side chamber or vice versa.

It is not always possible to carry out the supply of the flushing liquid in accordance with the uplift of the air at the lower connector of the dialyzer during the flushing of the dialyzer. The flushing thus takes place against gravity from top to bottom in the dialyzer chamber. In this respect, the displaced volume is taken along with the conveyed volume.

The duration of the flushing and the quantity of the flushing volume depend on a number of parameters. A larger chamber volume of the dialyzer and a smaller volume flow of the flushing liquid increase the flushing duration required for the venting. In currently known processes for venting, a fixedly preset flushing volume is used and it is assumed that the venting of the dialyzer is complete when this flushing volume has been conducted through the dialyzer. It is also known to flush for a preset time, e.g. for five minutes, and then to assume that a venting has taken place after this time period has elapsed.

It is a disadvantage in the known procedures that a complete removal of air from the dialyzer is sometimes not always given. A check of the remaining air quantity in the dialyzate-side chamber of the dialyzer does not take place in processes known from the prior art. On the other hand, the case can occur that, in known processes, flushing is carried out for longer or a larger flushing volume is used than would be necessary per se for the venting of the dialyzer.

It is therefore the underlying object of the present invention to further develop a method of the initially named kind such that the flushing process is optimized with respect to the quantity of the flushing liquid and/or with respect to the duration of the flushing process over known procedures.

The objection is satisfied by a method having the features described below. Provision is accordingly made that at least one property of the flushing liquid is measured at the outlet of the dialyzer or downstream of the dialyzer in the dialysate-side circuit to obtain one or more outlet-side measured values, with the measured property depending on the quantity of the air in the flushing liquid.

This measured property can, for example, be the conductivity of the flushing liquid, in particular the electrical conductivity of the flushing liquid, the sound speed at which the sound propagates in the flushing liquid or also an optical property of the flushing liquid. Other properties or parameters which depend on the air quantity of the flushing liquid are also suitable for the method.

It is particularly advantageous if the measured property represents the conductivity of the flushing liquid. As a rule, conductivity sensors which can be used for the present method are anyway located in the hydraulic system of blood treatment devices, i.e. in the dialysis circuit.

A preferred embodiment of the invention is thus that air is removed from the dialyzate-side chamber of the dialyzer via the hydraulic system of a blood treatment device, i.e. via the dialyzate-side circuit, and this air is transported off with the flushing liquid via the hydraulic system. As a rule, conductivity sensors or conductivity cells are located in the dialyzate-side circuit which monitor the conductivity of the dialysis solution in the treatment operation of the dialysis. The air flowing past the conductivity cells results in a considerable reduction of the conductivity of the air/liquid mixture determined in the flushing liquid. The conductivity or the property of the air/liquid mixture can be determined during the flushing process of the dialyzer by means of the conductivity cells or other sensors by means of which a property of the flushing liquid can be measured which depends on the air quantity and a check can be made whether the air portion in the flushing liquid or in the mixture of air and flushing liquid is reduced, from which a conclusion can be drawn on an escaping air removal from the dialyzate-side chamber of the dialyzer.

The flushing process can then be ended automatically by the device or manually on the basis of the outlet-side measured value or values and/or a signal can be given that the flushing process is ended.

Provision is made in a preferred embodiment of the invention that at least one property of the flushing liquid is likewise measured at the inlet of the dialyzer or upstream of the dialyzer in the dialyzate-side circuit to obtain one or more inlet-side measured values, wherein the property depends on the quantity of the air in the flushing liquid and wherein the inlet-side measured value or values are compared with the outlet-side measured value or values.

This outlet-side measured property is the same property as the inlet-side measured property, i.e., for example, the conductivity of the flushing liquid, etc.

If the inlet-side measured values and the outlet-side measured values are close to one another or if they coincide, a conclusion can be drawn that there is no longer any air in the dialyzate-side chamber and the flushing process is therefore ended or it is at least correspondingly signaled that it can be ended.

It is conceivable that the flushing process is ended or that a sufficient flushing is signaled or that a conclusion thereon is drawn when the outlet-side measured values are constant or lie in a specific tolerance range. The outlet-side measured values show high fluctuations at the start of the flushing process. The conductivity of the air/liquid mixture which flows from the dialyzate-side chamber at the start of the flushing process is thus close to zero or is zero and only stabilizes after a certain flushing time. This is due to the fact that it takes a certain time until the air is completely displaced from the dialyzate-side chamber so that ultimately the conductivity or another property of the flushing liquid, which is largely or completely air-free, is measured at the outlet side.

It is furthermore conceivable that the flushing process is ended or a sufficient flushing is signaled or a conclusion thereon is drawn when the standard deviation of the outlet-side measured values is below a certain limit value or does not exceed a certain limit value or lies within a certain tolerance range. If the standard deviation of the measured values is small, it can be concluded that the outlet-side measured values have sufficient stability and that a large or complete venting of the dialyzate-side chamber has taken place.

Provision is made in a further embodiment of the invention that the flushing process is ended or a sufficient flushing or a conclusion thereon is drawn when the expected value of the outlet-side measured values lies within a certain tolerance range and/or when the difference of the expected values of the outlet-side measured values and of the inlet-side measured values are below a specific limit value or do not exceed a certain limit value. The term "expected value" is preferably to be understood as an average value over a plurality of measured values which are preferably detected in a window moving in time.

It is conceivable that the expected value of the outlet-side measured values lies within a certain tolerance range—on the measurement of the conductivity e.g. in a tolerance range in the range of 0.1 mS/cm. It is also conceivable that the difference of the expected values is determined at the inlet side and at the outlet side and that a check is made whether it is within a certain tolerance range.

Provision is made in a further embodiment of the invention that the quotient is determined from the difference of the measured property and of the same property with a completely ventilated dialyzate-side chamber and from the difference of this property with a completely vented property and a completely ventilated property. The flushing process can then be ended on the basis of this value or a sufficient flushing can be signaled or a conclusion can be drawn thereon in dependence on the value which the quotient adopts.

Provision is made in a further embodiment of the invention that the volume flow with which the flushing liquid flows through the dialyzate-side chamber is constant in time or is also variable in time. A time-variable conveying rate is advantageous to facilitate the taking along of air bubbles with the help of turbulences which occur in the dialyzer chamber.

The present invention furthermore relates to an apparatus having the features described below. Provision is made therein that at least one sensor is arranged at the outlet of the dialyzer or downstream of the dialyzer in the dialyzate-side circuit, the sensor measuring the named property of the flushing liquid such as a conductivity or another property which depends on the quantity of the air in the flushing liquid.

As stated, the property can be the speed of sound, the conductivity or also an optical property of the flushing liquid.

The apparatus preferably has an evaluation unit which is configured such that it ends the flushing process and/or signals that it can be ended on the basis of the measured value or values.

In addition, at least one further sensor can be arranged at the inlet of the dialyzer or upstream of the dialyzer, the sensor measuring the same property of the flushing liquid at the inlet side. At least one evaluation unit can furthermore be provided which carries out a comparison between the inlet-side measured value or values and the outlet-side measured value or values.

This evaluation unit can be configured such that it ends the flushing process or initiates its end or signals a sufficient flushing when the outlet-side measured values are constant or lie in a certain tolerance range.

The evaluation unit can be configured such that the flushing process is ended or a sufficient flushing is signaled when the standard deviation of the outlet-side measured values is below a certain limit value or does not exceed a certain limit value or lies within a certain tolerance range.

The evaluation unit can furthermore be configured such that the flushing process is ended or that its end is initiated or a sufficient flushing is signaled when the expected value of the outlet-side measured values lies within a certain tolerance range and/or when the difference of the expected values of the outlet-side measured values and of the inlet-side measured values is below a certain limit value or does not exceed a certain limit value.

Provision is made in a further embodiment of the invention that at least one evaluation unit is provided which is configured such that the quotient is determined from the difference of the measured properties and of this property with a completely ventilated dialyzate-side chamber and the difference of the property with a completely vented and completely ventilated chamber and such that the flushing process is ended or a sufficient flushing is signaled on the basis of the value of this quotient.

Provision can furthermore be made that the apparatus has at least one pump which is configured such that it conveys the flushing liquid through the dialyzate-side chamber, with this pump being able to be configured or being operated so that the conveying rate of the flushing liquid is constant in time or variable in time.

The invention furthermore relates to a blood treatment device, in particular to a dialysis machine, having at least one apparatus in accordance with the following description.

It is pointed out that the term "dialyzer" is here not necessarily limited to a dialyzer which is used within the framework of a hemodialysis treatment. The term also includes filters which are used with other blood treatment processes such as in hemodiafiltration.

Figure 2:
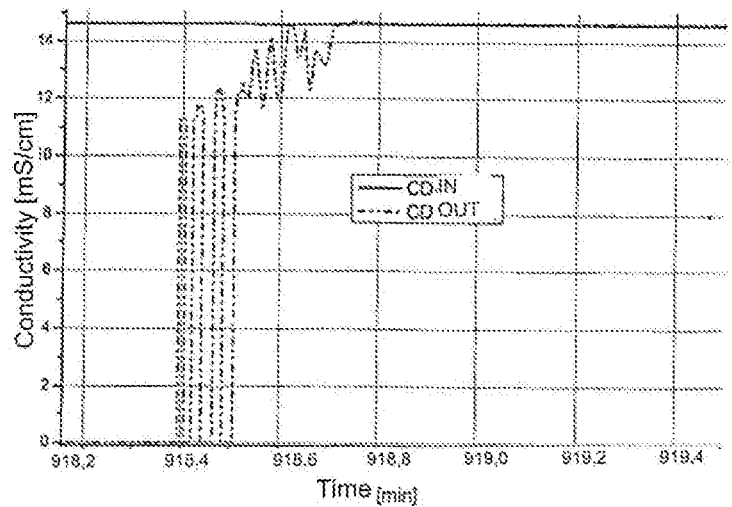
Figure 3:
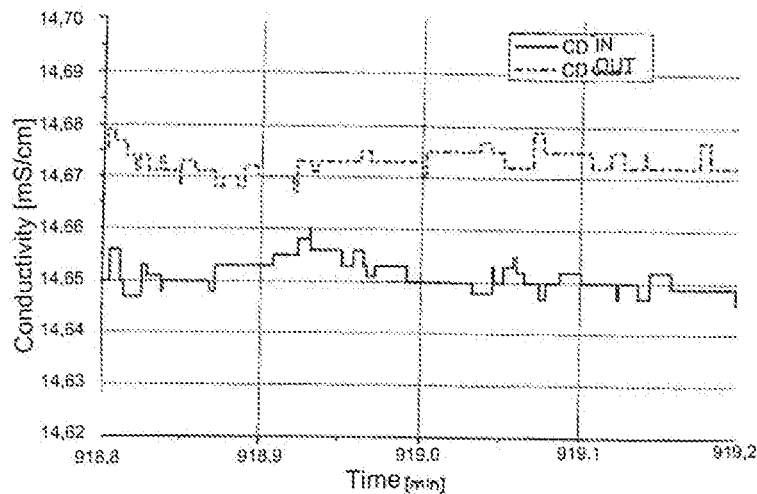

Further details and advantages of the invention will be explained in more detail with reference to an embodiment shown in the drawing. There are shown:

FIG. 1: a schematic view of a dialyzer having the dialyzate-side circuit as well as conductivity sensors in the dialyzate-side feed line and in the dialyzate-side drain line;

FIG. 2: the time development of the conductivity measured by means of the sensors in accordance with FIG. 1 during the flushing process; and FIG. 3: the time development of the conductivities measured by the sensors in accordance with FIG. 1 during the flushing process with sufficient venting.

FIG. 1 shows a dialyzer 10 as well as a part of the hydraulic system or of the dialyzate-side circuit in the form of the feed line 12 and the drain line 14. In accordance with the arrow direction shown, flushing liquid is led into or led out of the dialyzate-side chamber through these lines. Dialysis solution is conducted to the dialyzer and from the dialyzer through these lines during the operation of a blood treatment device.

The two lines 12, 14 are in fluid communication with a dialyzate-side chamber of the dialyzer. It is separated from a blood-side chamber of the dialyzer by one or more membranes, preferably by a hollow fiber bundle. The blood-side inflows or outflows of the dialyzer which are connected to the blood-side chamber are marked by the reference numerals 16 and 18 in FIG. 1.

As can be seen from FIG. 1, a respective conductivity measuring cell 12', 14', which measure the conductivity of the flushing liquid before the dialyzer 10 and also after the dialyzer 10, are both located in the feed line 12 and in the drain line 14. In treatment operation, these conductivity sensors 12', 14' serve the measurement of the conductivity of the dialysis solution.

The conductivity of the air/liquid mixture during the flushing process of the dialyzer can be determined by means of the conductivity cells 12', 14' and a check can be made whether the air portion in the mixture is reduced, from which a conclusion can be drawn on a sufficient air removal from the dialyzate-side chamber of the dialyzer 10.

The measurement of the conductivity or of another property which depends on the presence of air in the dialysis solution or flushing liquid is determined either continuously in time or at a plurality of points in time.

FIG. 2 shows the conductivities of the flushing liquid flowing into the dialyzate-side chamber of the dialyzer 10 (CD IN) and of the flushing liquid flowing out of the dialyzate-side chamber of the dialyzer 10 (CD OUT) during the flushing process.

As can be seen from FIG. 2, the conductivity of the flushing liquid flowing into the dialyzer chamber shows a constant value of 14.6 mS/cm, while the conductivity of the air/liquid mixture flowing out of the dialyzer first has no conductivity and then has substantial fluctuations. The conductivity of the flushing liquid flowing out of the dialyzer only stabilizes after a certain flushing time since the quantity of the air which is taken along with the flushing liquid reduces over the course of the flushing process.

The status of the dialyzer filling or of the air removal can preferably be checked in connection with a variable volume rate for the efficient flushing of the dialyzer chamber with reference to the analysis of the conductivities or of another suitable parameter of the inflowing or outflowing flushing liquid.

As can be seen from FIG. 2, the conductivities at the inflow side and at the outflow side equalize toward the end of the flushing process.

FIG. 3 shows the curve of the conductivities as in FIG. 2 from a time onward at which the filling has been successfully ended or the air removal has taken place. As can be seen from FIG. 3, it results that the fluctuations are small at the outlet side and furthermore that the difference between the inlet-side measured values and the outlet-side measured values is likewise small.

The flushing process preferably takes place with a variable flushing volume conveying i.e. with a variable conveying rate of the flushing liquid for generating turbulences in the dialyzer. A constant conveying rate is, however, also covered by the invention.

Provision is made in a conceivable embodiment of the invention that the flushing procedure is ended or that it is correspondingly signaled that it can be ended when the outlet-side measured value in the outflowing air/liquid mixture or in the outflowing flushing liquid largely corresponds to the inlet-side measured value. On a successful filling procedure, no more air is transported out of the dialyzer so that the conductivity of the liquid flowing out of the dialyzer is stable. It can be understood by this that there is a small standard deviation over the statistical expected value. The standard deviation is suitable as a quality parameter for an evaluation of the successful venting. The standard deviation can be determined while taking account of an expected value $X_C$.

It has proved to be meaningful to calculate the expected value $X_C$ and a standard deviation $\sigma_c$ within a window moving in time with N sampling elements or measured points both for the inflowing liquid and for the outflowing liquid:

$$\langle X_C \rangle = \frac{1}{N} \sum_{i=1}^{N} c_i; \; \sigma_C = \frac{1}{N} \sqrt{\sum_{i=1}^{N} |\langle X_C \rangle - c_i|^2}$$

The expected values of the conductivity of the inflow and outflowing flushing liquid should coincide within a tolerance range, for example in the order of 0.1 mS/cm. The deviations $\sigma_C$, which are a measure for the stability of the conductivity over time, should also lie within a narrow range (e.g. 0.05 mS/cm) in a comparison of the inflowing or outflowing liquid. I.e. the two standard deviations of the inlet-side measured values and of the outlet-side measured values should likewise coincide or their differences should lie within the named tolerance range.

The venting procedure can be aborted when a certain quality of the venting has been reached. This can be the case when both the expected values and the deviations of the conductivity of the inflowing or outflowing flushing liquid lie within a tolerance range defined by the quality.

These statements naturally do not only apply to the conductivity, but also to any desired other measurement parameter which represents a measure for the presence of air in the flushing liquid.

As initially stated, alternative methods for detection can also be used in addition to the detection of air segments in the conductive liquid by means of conductivity sensors. The measurement of the sound of speed, which is considerably different in air and in liquid, can be considered, for example. An ultrasound detector can thus also be used as the sensor which is used alternatively or additionally to the conductivity sensors.

It is conceivable that the sound transit time of sound pulses is analyzed, for example within a certain volume flowing through the sound sensor, and that the ratio of the determined mean transit time v less the sound transit time in completely ventilated paths $v_{air}$ is set to the transit time difference between completely ventilated and completely vented paths $v_{liquid}$:

$$\Phi[\%] = \frac{v - v_{Luft}}{v_{Flüssig} - v_{Luft}} \times 100$$

This ratio in percent is a measure for the degree of venting of the dialyzer. If the ratio is 100%, the determined mean transit time v corresponds to the transit time with a completely vented path $v_{liquid}$, i.e. a conclusion can be drawn that a complete venting has taken place.

This procedure naturally also does not only relate to the speed of sound as a measurement value, but can also be used for any other measurement value.

Optical analyses of the degree of venting are also conceivable in addition to sound analyses. Since the dielectricities between aqueous solutions and air differ considerably for many optical frequencies, the degree of venting can also be determined by means of optical measurement methods and a decision can thereupon be made that the flushing process can be terminated or ended.

The invention claimed is:

1. A method of flushing a dialyzer with a flushing liquid, wherein the dialyzer is arranged in a dialyzate-side circuit of a blood treatment device and wherein the dialyzer has at least one dialyzate-side chamber which has at least one inlet and at least one outlet for the flushing liquid and which is flowed through by the flushing liquid, the method comprising measuring multiple times in a time window moving in time a property of the flushing liquid related to the quantity of air in the flushing liquid at the outlet of the dialyzer or downstream of the dialyzer in the dialyzate-side circuit to obtain multiple outlet-side measured values and averaging the multiple outlet-side measured values to obtain an expected value of the outlet-side measured values, measuring multiple times in a time window moving in time the property of the flushing liquid related to the quantity of air in the flushing liquid at the inlet of the dialyzer or upstream of the dialyzer to obtain one or more inlet-side measured values and averaging the multiple inlet-side measured values to obtain an expected value of the inlet-side measured values, comparing the expected inlet-side measured value with the expected outlet-side measured value and concluding the flushing process is finished when the difference between the expected value of the outlet-side measured values and the expected value of the inlet-side measured value is below a specific limit value or does not exceed a certain limit value, determining a quotient from the difference of the measured property and of this property with a completely ventilated dialyzate-side chamber and the difference from the property with a completely vented and a completely ventilated chamber, and, based on the determined quotient, ending the flushing process, signaling a sufficient flushing, or drawing a conclusion.

2. A method in accordance with claim 1, characterized in that the conductivity of the flushing liquid or the speed of sound at which sound propagates in the flushing liquid or an optical property of the flushing liquid is measured.

3. A method in accordance with claim 1, characterized in that the flushing process is ended or that a sufficient flushing is signaled or a conclusion thereon is drawn when the expected value of the outlet-side measured values lies within a certain tolerance range and/or when the difference of the expected values of the outlet-side measured values and of the inlet-side measured values is below a specific limit value or does not exceed a certain limit value.

4. A method in accordance with claim 1, characterized in that the volume rate at which the flushing liquid flows through the dialyzate-side chamber is constant in time.

5. A method in accordance with claim 1, characterized in that the volume rate at which the flushing liquid flows through the dialyzate-side chamber is variable in time.

* * * * *